(12) United States Patent
Hardy et al.

(10) Patent No.: US 9,750,843 B2
(45) Date of Patent: Sep. 5, 2017

(54) HAEMOSTATIC MATERIAL

(75) Inventors: Craig Hardy, Cheshire (GB); Andrew Darby, Stoke on Trent (GB); Guy Eason, Cheshire (GB)

(73) Assignee: MEDTRADE PRODUCTS LIMITED, Crewe Cheshire (GB)

( * ) Notice: Subject to any disclaimer, the term of this patent is extended or adjusted under 35 U.S.C. 154(b) by 0 days.

(21) Appl. No.: 12/988,332

(22) PCT Filed: Apr. 27, 2009

(86) PCT No.: PCT/GB2009/001065
§ 371 (c)(1),
(2), (4) Date: Nov. 18, 2010

(87) PCT Pub. No.: WO2009/130485
PCT Pub. Date: Oct. 29, 2009

(65) Prior Publication Data
US 2011/0052665 A1 Mar. 3, 2011

(30) Foreign Application Priority Data
Apr. 25, 2008 (GB) ................... 0807561.6

(51) Int. Cl.
| | | |
|---|---|---|
| *A61L 15/00* | (2006.01) | |
| *A61L 26/00* | (2006.01) | |
| *A61L 15/28* | (2006.01) | |
| *A61L 15/48* | (2006.01) | |
| *A61L 15/58* | (2006.01) | |
| *A61L 15/62* | (2006.01) | |
| *A61K 31/715* | (2006.01) | |
| *A61K 31/722* | (2006.01) | |

(52) U.S. Cl.
CPC ........ *A61L 26/0023* (2013.01); *A61K 31/715* (2013.01); *A61K 31/722* (2013.01); *A61L 15/28* (2013.01); *A61L 15/48* (2013.01); *A61L 15/58* (2013.01); *A61L 15/62* (2013.01); *A61L 26/0061* (2013.01); *A61L 2300/418* (2013.01); *A61L 2300/608* (2013.01); *A61L 2400/04* (2013.01); *Y10T 156/10* (2015.01)

(58) Field of Classification Search
CPC combination set(s) only.
See application file for complete search history.

(56) References Cited

U.S. PATENT DOCUMENTS

| | | | |
|---|---|---|---|
| 5,836,970 A | 11/1998 | Pandit | |
| 5,851,461 A * | 12/1998 | Bakis et al. | 264/50 |
| 6,998,509 B1 | 2/2006 | Nielsen | |
| 7,981,872 B2 * | 7/2011 | Hardy et al. | 514/55 |
| 8,106,030 B2 * | 1/2012 | Hardy et al. | 514/55 |
| 2003/0091851 A1 | 5/2003 | Khor et al. | |
| 2005/0123588 A1 * | 6/2005 | Zhu et al. | 424/443 |
| 2005/0203058 A1 * | 9/2005 | Johnson | 514/55 |
| 2006/0210613 A1 * | 9/2006 | Carliss | 424/448 |
| 2006/0257458 A1 | 11/2006 | Gorman et al. | |
| 2007/0009581 A1 | 1/2007 | Carlucci et al. | |
| 2007/0051376 A1 * | 3/2007 | Kulichikhin et al. | 128/894 |
| 2007/0255192 A1 | 11/2007 | Patel et al. | |

FOREIGN PATENT DOCUMENTS

| | | |
|---|---|---|
| EP | 0340945 A1 | 11/1989 |
| EP | 0596215 A1 | 5/1994 |
| GB | 2095995 A | 10/1982 |
| GB | 2129300 A | 5/1984 |
| GB | 2393120 A | 3/2004 |
| GB | 2432790 A | 6/2007 |
| GB | 2435425 A | 8/2007 |
| WO | 02102276 A2 | 12/2002 |
| WO | 2006097940 A1 | 9/2006 |
| WO | 2007009050 A2 | 1/2007 |
| WO | 2007095005 A1 | 8/2007 |
| WO | WO 2008019129 A2 * | 2/2008 |
| WO | 2008054566 A1 | 5/2008 |

OTHER PUBLICATIONS

Visavarungroj et al, Crosslinked Starch as Binding Agent: I. Conventional Wet Granulation, vol. 59, Issue 1, pp. 73-78 (Abstract Only) (1990).*
Fan Y et al: "Haemostatic efficacy of an ethyl-2-cyanoacrylate-based aerosol in combination with tourniquet application in a large wound model with an arterial injury" Injury, John Wright and Sons, Bristol, GB LNKD-DOI:10.1016/J.INJURY.2007.10.004, vol. 39, No. 1, Jan. 1, 2008 (Jan. 1, 2008), pp. 61-66.
Eric Dickinson: "Clotting Agents" Law Officer, vol. 4, No. 3, Mar. 2008 (Mar. 2008), pp. 32-36.
Kozen Buddy G et al: "An alternative hemostatic dressing: comparison of CELOX, HemCon, and QuikClot." Academic Emergency Medicine : Official Journal of the Society for Academic Emergency Medicine Jan. 2008 LNKD-Pubmed:18211317, vol. 15, No. 1, Jan. 2008 (Jan. 2008), pp. 74-81.
Okamoto Y. et al: 'Effects of chitin and chitosan on blood coagulation.' Carbohydrate Polymers vol. 53, No. 3, Aug. 15, 2003, Applied Science Publishers, Ltd. Barking, GB, pp. 337-342.
Ward, Owen P., Bioprocessing, Van Nostrand Reinhold, 1991 ed., pp. 57-60.

\* cited by examiner

*Primary Examiner* — Dennis J Parad
(74) *Attorney, Agent, or Firm* — Barlow, Josephs & Holmes, Ltd.

(57) ABSTRACT

The present invention relates to a haemostatic material comprising a carrier layer and a material for wound contact comprising at least one haemostat in particulate, granular, powder, flake or short fibrous form. Such a haemostatic material is useful, for example, in reducing or stopping bleeding of a physiological target site in a person or animal, and can also be used to stem bleeding during medical procedures.

31 Claims, 8 Drawing Sheets

HAEMOSTATIC MATERIAL

CROSS-REFERENCE TO RELATED APPLICATIONS

This patent document is a national phase application filed pursuant to 35 U.S.C. §371 of PCT International Application No. PCT/GB2009/001065, filed on Apr. 27, 2009, which claims priority to earlier filed British Patent Application No. 0807561.6, filed on Apr. 25, 2008.

BACKGROUND OF THE INVENTION

1. Field of the Invention

The present invention relates to a haemostatic material. Haemostatic materials are useful, for example, in reducing or stopping bleeding of a physiological target site in a person or animal. The material can also be used to stem bleeding during medical procedures.

2. Background of the Related Art

There are many circumstances in which animals, both human and non-human, may become injured or wounded causing bleeding. In the case of minor wounds, the bleeding may be stemmed by the natural haemostatic mechanisms of the body which lead to coagulation of the blood to form solid clots which prevent hemorrhage and aid repair of damaged blood vessels. Basic first aid may be administered in some cases to stem blood flow and assist wound healing, such as stemming blood flow in a patient by the application of continuous pressure to a wound. This enables clotting factors to collect at the site of the wound and form a congealed blood mass to stem blood flow. However, this technique is not suitable for severe wounds and wounds having multiple bleeding points. Therefore, bleeding out continues to be a major cause of death.

Death caused by bleeding out is a particular problem in environments such as battlefields. Typically, wounds arising in such situations are accompanied by significant bleeding, and many result in death. Bleeding out is also a significant cause of death amongst the civilian population following trauma injuries.

In attempts to provide products which facilitate the stemming of blood flow from a wound, haemostatic products have been developed.

Haemostatic agents are typically presented in the form of solid powders or granules, or as liquids. All of these forms, being flowable, provide for good contact with the irregular surfaces which are typical of wounds so that good haemostasis can be achieved. However, the flowable nature of particulate of liquid haemostatic agents also renders them relatively difficult to handle in use. It can be a problem to retain the flowable haemostatic agent at the wound site where the stemming of blood flow is required.

These agents include a product sold under the brand name QuikClot®. QuikClot® comprises a zeolite compound which absorbs water from the blood flowing from a wound such that the clotting factors present in the blood become concentrated and the blood coagulates more quickly, so the zeolite and the coagulated blood together form a coagulum to stem blood flow.

In a development of this product, a gauze bag is provided in which the haemostatic agent is contained. Whilst this improves the ease of handling and application of the haemostat, the gauze bag physically separates the haemostat from the body tissues and blood at the wound site. This reduces the efficacy of the haemostat. Further, although the gauze bag is flexible, the particles of haemostatic agent are unable to move outside the bag and into any crevices or irregular surfaces of the wound, as the holes in the gauze bag are smaller than the typical particle size of the haemostatic agent retained in the gauze bag. The gauze bag remains in situ until removed.

A further product is described in WO 02/102276. The product is a flat single piece sheet dressing comprising a chitosan layer. It does not include granules or flakes as the wound contact layer. The dressing is applied to the site of a wound and forms a seal. The chitosan causes the blood to coagulate which together with the seal formed by the sheet stems the blood flow. However, such products must be applied directly to the source of bleeding, i.e. to an artery. Such application requires skill and accuracy. Military medics and first responders do not have the necessary skills to identify the source of bleeding and apply the dressing thereto. In any event, it would be extremely difficult to perform such a delicate operation on a battlefield or at a trauma site. In addition, when the sheets according to WO 02/102276 are removed, bleeding restarts as the sealing layer is removed.

GB 2095995 and GB 2129300 disclose the use of pure chitosan acetate as a haemostatic material. However, the gel which forms from the pure salt is very thin as only the outermost surface of the material is available to act in a short period of time. Quite often this material fails to stop bleeding and even when it does, the clot is very thin and weak so that when the patient is moved, the clot is compromised and bleeding resumes.

Therefore, it is an object of the present invention to provide a haemostatic material which stems the flow of blood from a physiological target site relatively quickly and which is easy and safe to use.

SUMMARY OF THE INVENTION

According to the present invention there is provided a haemostatic material comprising a carrier layer and a material for wound contact comprising at least one haemostat in particulate, granular, powder, flake or short fibrous form.

By "haemostat" it is meant any agent which is capable of producing a clot or plug which stops or reduces bleeding when it comes into contact with blood.

The physiological target site may be any site in or on the body of an animal. The animal may be a human or a non-human animal. The physiological target site may be a wound or it may be an opening in a body caused during a medical procedure, for example during surgery. Hereinafter, the physiological target site is referred to as a wound for convenience and illustrative purposes only.

The haemostatic material of the present invention can be applied by a person with only basic medical training. It is a matter of simply applying the material to the physiological target site followed by pressure.

Advantageously, the haemostatic material according to the present invention is easy to handle and apply. It is typically stored dry prior to application.

Products which take advantage of biological processes tend to be temperature dependent. Often patients suffering blood loss are either very hot due to exertions on the battlefield or very cold as they have been exposed to cold conditions. Currently available products are less effective at such temperature extremes. Advantageously, the material of the present invention is not affected by temperature fluctuations and therefore works equally well at temperatures both above and below normal body temperatures (37° C.).

The haemostatic material according to the invention may have different forms. According to one aspect of the invention, the haemostat may be bonded to the carrier layer using heat and/or pressure.

According to another aspect, the haemostat may be bonded to the carrier layer using an adhesive comprising a bonding agent, which may form a layer between the haemostat and the carrier layer wherein the haemostat and any adhesive constitute separate discrete layers.

According to another aspect, the adhesive and haemostat may be mixed together and located on the carrier layer.

According to another aspect, both sides of the carrier layer are at least partially coated with the haemostat. The haemostat is typically bonded to the carrier layer in the same manner on both sides.

According to a further aspect, there may be a further layer on top of the mixed adhesive/haemostat layer, or on top of the separate adhesive and haemostat layers, or on top of the haemostat layer which is bonded to the carrier layer by heat and/or pressure, the further layer comprising a soluble, dispersible or removable retaining material. This material is dissolved or degraded by, or dispersed in, bodily fluids when the haemostatic material is applied to a wound.

This further layer can also be used to retain the haemostat. It may a soluble film made from a polysaccharide such as gelatine or a cellulose derivative, or it may be made from a soluble film-former such as polyvinyl acetate (PVA) or polyvinyl alcohol (PVOH).

A dispersible film would typically contain a water-soluble material such as those listed above as well as other insoluble materials, such as cellulose fibres, and would disperse when wet. A removable layer could any sheet or net which could be peeled off prior to use.

By soluble or dispersible it is meant that the layer is soluble or dispersible under conditions encountered upon contact with a wound site in an animal body, such as a temperature between about 32 to about 45° C. and the nature and pH of the bodily fluids contacted. The layer is typically substantially completely soluble or dispersible under such conditions. Specifically, the layer is soluble in water or an aqueous liquid, and/or it degrades and disperses in water or an aqueous liquid. The terms soluble and dispersible are not mutually exclusive. The soluble, dispersible or removable retaining layer is most typically formed from a material which is susceptible to metabolisation within a human or animal body.

According to a further aspect, there may be a mixed adhesive/haemostat layer situated on both an upper and lower surface of the carrier layer, these being the two larger surfaces of the material as it is typically in a sheet form. This allows for more effective reduction or stopping of blood flow in wounds which it is possible to close around the material of the invention. Alternatively, the separate adhesive and haemostat layers may be situated on both the upper and lower surfaces of the carrier layer, or haemostat may be bonded by heat and/or pressure to both the upper and lower surfaces of the carrier layer.

The further layer comprising a soluble, dispersible or removable retaining material may be present on one or both surfaces in all of the instances where the adhesive and haemostat are present as separate layers on one or both surfaces, or are present as a mixed adhesive/haemostat layer on one or both surfaces, or also if there is no adhesive and the haemostat was bonded to the carrier layer using heat and/or pressure on one or both surfaces.

The haemostat may also be incorporated into the further layer comprising a soluble, dispersible or removable retaining material.

According to one embodiment of the invention, the haemostat material will have two identical sides. This can be achieved by treating each side individually with the same process, or by treating both sides at the same time.

According to another embodiment, the bonding agent is chosen so that even when it is wet with blood, at least a portion of the haemostat will remain in an area of bleeding even when the carrier layer is removed. Previously developed haemostatic materials do not leave any haemostat at the wound site once the material is removed, so bleeding resumes.

This can be achieved by having the haemostat bonded so that it is released from the bonding layer when it gets wet. This is effective if the bonding layer or the haemostat is sufficiently water sensitive to weaken the bond when the combination is wet. The adhesive does not have to dissolve to allow this, but rather just weaken or change shape.

The bonding agent is typically at least partially soluble in bodily fluid conditions such as blood and also does not cause significant detrimental effects to the human or animal body being treated.

According to one embodiment of the invention, the haemostat is a polysaccharide or a chitosan salt. Chitosan is a derivative of solid waste from shell fish processing and can be extracted from fungus culture. It is a water insoluble cationic polymeric material. Therefore, chitosan for use with the present invention is first converted into a water soluble salt. Therefore, the chitosan salt is soluble in blood to form a gel which stems blood flow.

Chitosan salts are ideally suited for the applications described herein as chitosan is readily broken down in the body. Chitosan is converted to glucosamine by the enzyme lysozyme and is therefore excreted from the body naturally. It is not necessary to take any measures to remove the chitosan from the body.

Furthermore, chitosan salts exhibit mild antibacterial properties and as such their use reduces the risk of infection.

Exemplary chitosan salts which are suitable for use with the present invention include, but are not limited to, any of the following either alone or in combination: acetate, lactate, succinate, malate, sulphate or acrylate. They are typically in powder form. The foregoing examples are provided by way of example only and are not intended to be limiting in any way.

Typically, the chitosan salt used in the present invention is chitosan succinate.

The chitosan salt is prepared by combining chitosan with an appropriate acid. It will be appreciated that the acid may be any inorganic or organic acid which yields a chitosan salt which is soluble under the conditions associated with a human or animal body, particularly in blood. Suitable acids would be recognised by a skilled person. For example, chitosan phosphate is insoluble in such conditions and so phosphoric acid is unsuitable.

According to one embodiment, the haemostat constitutes at least about 5% by weight of the haemostat, or more typically at least about 20% by weight.

The haemostat is typically granular, or it can comprise short fibres no more than about 7.5 mm in length, more typically no more than about 5 mm in length.

The adhesive layer, when present, comprises a bonding agent for binding the haemostat to the carrier layer. Typically the bonding agent is a meltable material.

Nonwoven fabrics are typically made using powder bonding, thermal bonding, physical and latex bonding. All of these processes could be adapted to bind the haemostat to the carrier layer.

Powder bonding uses meltable powders are often polyester, polypropylene, acrylic or polyethylene based. Thermal bonding uses meltable fibres such as those which are polypropylene, polyester or polyethylene-based. Latex bonding uses liquid latex adhesive which can be acrylic based, for example. Physical bonding occurs when materials are physically entangled or pushed together by a force such as pressure.

Typical materials include, but are not limited to, low melt copolyester resins and Delnet, which is a meltable net provided by DelStar Technologies, Inc.

According to one embodiment, the carrier layer comprises a viscose non-woven material, or alternatively it may comprise a woven gauze, a film, a foam, or a sheet gel. The material of the carrier material may or may not be degradable in conditions associated with wounds in or on a human or animal body. However, according to one embodiment of the invention, the material of the carrier material is safely degradable in the body so that the whole haemostatic material piece can be left in place after surgical use or treatment. Examples of safe and degradable materials include, but are not limited to, oxidised cellulose, collagen, polycaprylactone, polylactide acid, polylactide-co-glycolide, polyglycolide, chitin, etc.

The material may take any suitable form and may be provided in a range of different sizes, shapes and thicknesses necessary to deal with a wound, such as square, rectangular, circular or elliptical. For example, the material may be a generally flat shape with little height relative to its width/depth. Any regular or irregular shape may be employed. It may be provided in large sheets which can be cut to the required size.

The thickness of the material may be varied between upper and lower limits as desired. The upper limit of the thickness is typically about 2 cm, down to a few microns, such as 5-10 microns. It is however important that the material is flexible so that it can be curved to fit the contours of the body, and it is typically easily curved to the extent that it can be wrapped around a tube of approximately 1 cm diameter or less.

According to one embodiment of the invention, the haemostatic material may further comprise a medical surfactant. By "medical surfactant" it is meant any surfactant which is pharmaceutically acceptable for contact with or administration to a human or animal body and does not cause any significant detrimental effects to the human or animal body. Exemplary medical surfactants for use in the present invention include any of the following either alone or in combination: block copolymers based on ethylene oxide and propylene oxide (e.g. BASF Pluronics®), glycerol, polyethylene glycol, propylene glycol, fatty acids such as lauric acid, oleic acid, other fatty acids and fatty acid salts, silicone based surfactants and emulsifiers. Laurie acid and oleic acid are typically used.

The medical surfactant typically constitutes from about 0.001 to about 10% by weight of the haemostat.

More advantageously, the medical surfactant constitutes from about 0.5 to about 1% by weight of the haemostat used in the present invention. Advantageously, the presence of a surfactant gives rise to excellent wetting out properties. The way in which the haemostat wets out is crucial to its performance. That is, the haemostat can absorb the blood too quickly and simply mix with the blood without sufficient gelation having occurred to form a gel clot which is capable of stemming blood flow. On the other hand, if the haemostat absorbs the blood too slowly gelation occurs in only a small amount of the haemostat, generally the first few millimeters depth of the haemostat closest to the wound site. In this case the gel clot which forms is not sufficiently dense to stem the blood flow for a sufficient period of time to allow the patient to be moved to a medical centre. Typically, such a gel clot will break up as the patient is moved and bleeding will resume.

Another factor which has been found to be important to the performance is the particle size of the haemostat used. The particle size is measured by the size of sieve through which it will go or is retained by.

According to one embodiment, when the haemostat is in particulate or granular form, it has an average particle size of greater than about 200 mesh such that it will not pass through a 200 mesh screen. The average particle size may typically be greater than about 100 mesh, still more typically greater than about 50 mesh, and it is not desired that the particles or granules are able to pass through a 40 mesh screen.

More advantageously, the particle size of the surfactant will be substantially equivalent to that of the haemostat. By "substantially equivalent" it is meant that the relative sizes of the particles do not differ by more than about 10%, more typically by more than about 5%. The optimum particle size is achieved by grinding the haemostat and sorting by any suitable means such as sieving. Such sizing processes are well known to those skilled in the art and will not be described further.

According to a further embodiment, an amount of at least one inert material may be added to the haemostatic material.

It has been found that by adding an amount of an inert material and/or of a medical surfactant to the haemostat, i.e. in effect diluting the quantity of haemostat, the performance of the haemostat is actually enhanced further. A combination of the inert material and the medical surfactant together is particularly advantageous as the presence of the inert material further enhances the properties of the medical surfactant, and vice versa. Typically, the inert material is granular.

The inert material may comprise any non-fast gelling haemostat, that is, a haemostat that gels within about 30 seconds to about 1 minute of application to a bleeding wound.

Exemplary inert materials include but are not limited to cellulose, fumed silica, sand, clay, alginate, microcrystalline cellulose, oxidised regenerated cellulose, polyethylglycol, guar gum, xanthan gum, chitosan, chitosan derivatives, chitin, sucrose, lactose, pectin, carboxymethylcellulose, ground corn meal, collagen, gelataine, polyvinylalcohol, acrylic acid, acrylate (co)polymers such as Carbopol®, crosslinked acrylic acid-based polymers, barium sulphate, clay, lactose, sucrose, starch, or combinations of any two or more thereof. Typically, one or more inert materials selected from chitosan, chitin and carboxymethylcellulose are used.

The inert material may be added to the haemostat in an amount up to about 95% by weight of the total composition, typically up to about 90% by weight, and more typically up to about 80% by weight.

The haemostat typically has a pH of from about 3.5 to about 8.0. The pH is largely dependent upon the particular haemostat used, as they each have a different pH.

The rate at which the soluble, dispersible or removable retaining material dissolves or disperses can vary within the terms of the present invention. When present, the greater the rate of dissolution or dispersal of the material(s), the greater the rate at which the haemostat is exposed or released upon contact with water or body fluid(s) to bring about the desired therapeutic effect.

In some circumstances, it may be desirable to have a short lag period before exposure or release of the haemostat following contact of the material with water or aqueous fluid(s), to allow handling time for positioning and if necessary re-positioning of the material at the target site.

The properties of the soluble, dispersible or removable retaining material may be varied by selecting different soluble or dispersible material(s) and/or different combinations thereof. Thus, material(s) or combinations thereof may be selected according to the desired rate of dissolution or dispersal, temperature sensitivity, pH sensitivity, etc. The thickness of the receptacle may also be varied to adjust the rate of release or exposure of the contained haemostat. Such selections will be within the normal understanding and capability of the skilled person.

It will be appreciated that the rate of dissolution or dispersal may vary with the temperature at the target site. The water-soluble or water-dispersible material(s) may be susceptible to dissolution or dispersal at temperatures of around 0 to around 100° C., such as around 45° C. or below, more preferably around 41° C. or below and most preferably around 37° C. or below.

By way of illustration only, it may be desirable that at body temperature the soluble, dispersible or removable retaining material begins to dissolve or disperse within around 1 second to around 120 seconds of exposure to water or aqueous fluid(s), such as within around 5 to around 120 seconds, preferably within around 60 seconds, and most preferably within around 30 seconds. Substantially complete dissolution or dispersal of the material may occur within around 1 second to around 30 minutes, such as within around 5 minutes, preferably within around 3 minutes, and most preferably within around 2 minutes.

The dissolution or dispersion of soluble, dispersible or removable retaining material may be pH dependant, providing for a material which has a pH-sensitive dissolution or dispersion rate. This may be used to keep the material from dissolving or dispersing until it is introduced to the body.

The material(s) forming the receptacle may also contain one or more of the following in any combination: plasticising agents (such as glycerol, propylene glycol, polyethylene glycol), insolubilising agents, solubilising agents, surfactants, dispersed insoluble materials, dispersion adding materials, casting aids, bonding aids, adhesives, or materials which render the receptacle susceptible to dispersion upon exposure to photochemical, ultraviolet, biological, or chemical sources.

Water-insoluble materials may also be present in the dispersible retaining layer. When such water-insoluble materials are present, these may comprise, for example, one or more of the following in any combination: cellulose, chitin, silica, water insoluble cellulose derivatives, calcium alginate, zeolite, sand, chalk, water-swellable compounds, and polymeric materials such as polyurethane or polyisobutylene. This list is not exhaustive.

An example of a suitable commercially available chitosan-based haemostat is Celox™ (MedTrade Products Limited).

When chitosan is used as the haemostat in the material of the invention, an active base is prepared by preparing a mixture of chitosan in particulate, granular, powder, flake or short fibrous form and an appropriate acid in a solvent in which the chitosan is insoluble (typically 80:20 ethanol: water). The solvent is evaporated to provide a substantially active base material. The active base material may then be combined with an inert material and/or a medical surfactant as desired to provide the haemostat.

The haemostatic material may be provided in a sterile or non-sterile form. Where the material is provided in a sterile form, sterilisation may be carried out using any of the conventionally known methods, such as gamma irradiation, electron beam treatment, heat treatment, etc. A material in a non-sterile form may be provided in combination with one or more preservatives.

According to another embodiment of the invention, there is further provided a compression bandage or emergency bandage system where the haemostatic sheet material is used as a front face of an absorbent pad. The haemostatic sheet material will permit any excess blood to pass through it where it will be absorbed by the absorbent pad behind.

According to another embodiment of the invention, there is further provided a compression bandage or emergency bandage system where the haemostatic sheet material is applied in a rolled or folded arrangement with the bandage so as to allow it to be easily packed into a deep wound prior to using the compression bandage. The roll of haemostatic material may or may not be actually attached to the bandage system.

According to another embodiment of the invention, there is further provided a form of the haemostatic material which is a thin, approximately 1 cm wide roll of the material which can be used for relatively minor wounds or for situations such as nose bleeds.

According to another embodiment of the invention, there is further provided a haemostatic material as herein described wherein the haemostatic material further comprises an amount of a material which is opaque to X-rays which would allow it to be detected if it were to be left in a wound after treatment or surgery.

According to another embodiment of the invention, there is further provided a haemostatic material as herein described wherein a small shaped piece of material—for example, approximately 1 inch by 1 inch (2.52 cm×2.52 cm)—is used to seal an artery after a vascular access operation.

According to another embodiment of the invention, there is further provided a haemostatic material as herein described wherein the material is used as the absorbent pad on a first aid plaster.

According to another embodiment of the invention, there is further provided a haemostatic material as herein described wherein the sheet material is provided with a hole located approximately centrally in it. The shape of the haemostatic material in such an embodiment may be approximately circular, but may be any shape as desired. The hole in the material enables the material to be used around access ports and tubes, leads etc. which are going into a human or animal body.

According to a further aspect of the invention, there is provided a method of manufacturing a haemostatic material comprising a carrier layer and a material for wound contact comprising at least one haemostat in particulate, granular, powder, flake or short fibrous form, comprising the steps of:
  i) providing a carrier layer; and
  ii) contacting a quantity of a haemostat to the carrier layer, wherein the haemostat is in particulate, granular, powder, flake or short fibrous form.

The haemostat may be maintained in contact with the carrier layer using an adhesive or by using heat and/or pressure.

The present invention also provides a method of reducing or stopping blood flow from a wound. Therefore, there is provided a method of reducing or stopping blood flow comprising the steps of cleaning a wound area where possible, applying to said wound area a haemostatic material wherein the haemostatic material comprises a carrier layer and a material for wound contact comprising at least one haemostat in particulate, granular, powder, flake or short fibrous form, and applying constant pressure to wound area until a gel clot forms.

Typically, the constant pressure is applied to the wound area for at least about 3 minutes.

The present invention also provides a haemostatic material comprising a carrier layer and a material for wound contact comprising at least one haemostat in particulate, granular, powder, flake or short fibrous form, for use in the manufacture of a haemostatic wound dressing.

According to a further aspect of the invention, there is provided a haemostatic wound dressing comprising a haemostatic material, wherein the haemostatic material comprises a carrier layer and a material for wound contact comprising at least one haemostat in particulate, granular, powder, flake or short fibrous form.

According to a further aspect of the invention, there is provided a use of a haemostatic material, wherein the haemostatic material comprises a carrier layer and a material for wound contact comprising at least one haemostat in particulate, granular, powder, flake or short fibrous form, in reducing or stopping blood flow from a wound. The haemostatic material of the invention is particularly effective in reducing or stopping blood flow from a wound. Only a fraction of a gram of haemostat is sufficient to seal a bleeding artery.

BRIEF DESCRIPTION OF THE DRAWINGS

The invention will now be described further by way of example with reference to the following examples and figures which are intended to be illustrative only and in no way limiting upon the scope of the invention.

DETAILED DESCRIPTION OF THE PREFERRED EMBODIMENTS

Figure 1:
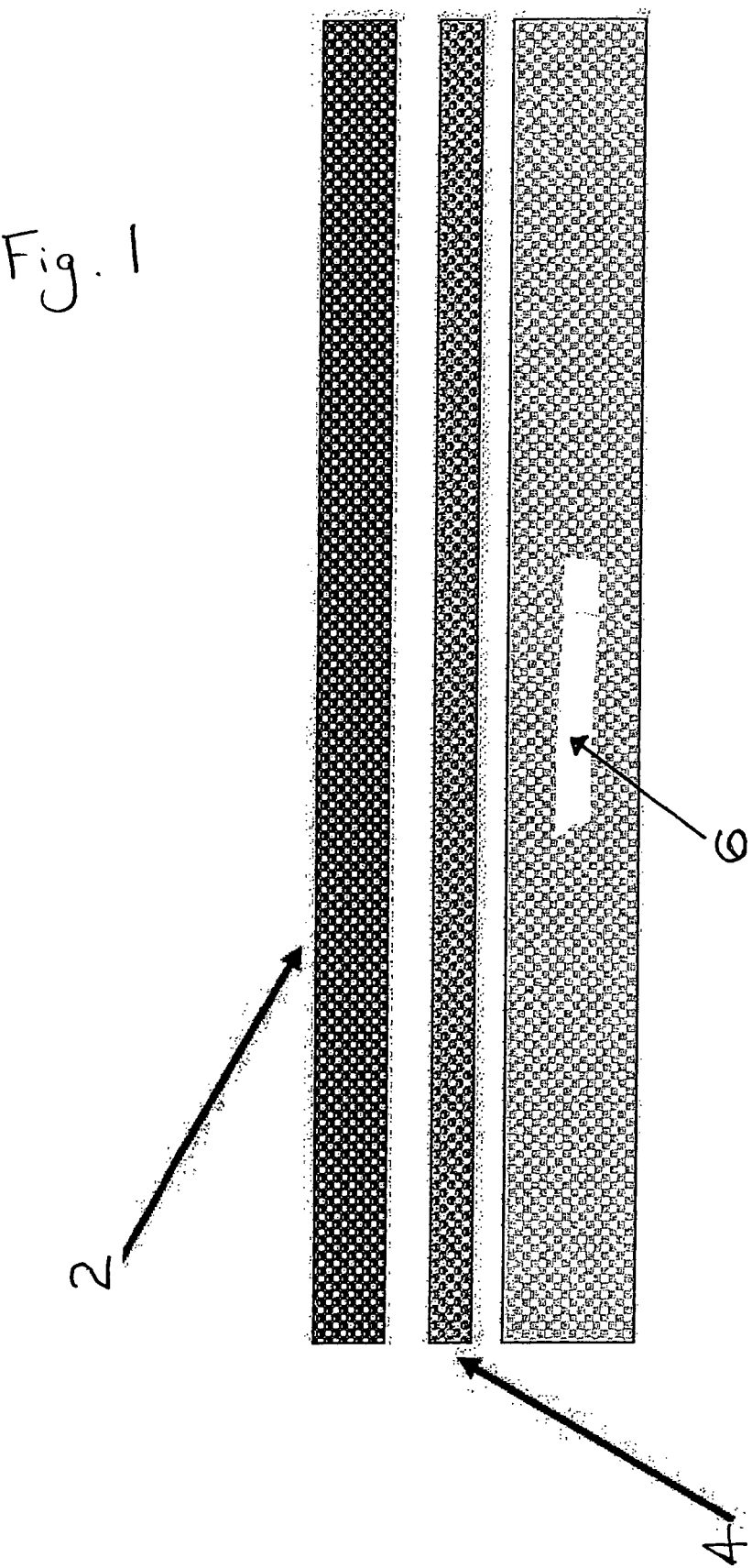
FIG. 1 shows a representation of a haemostatic material according to the invention having an adhesive layer and a haemostat as separate layers.

FIG. 1 shows the haemostat 2 located on top of the adhesive layer 4 which is in turn located on the carrier layer 6. In this embodiment, the adhesive layer and the haemostat constitute separate and distinct layers.

Figure 2:
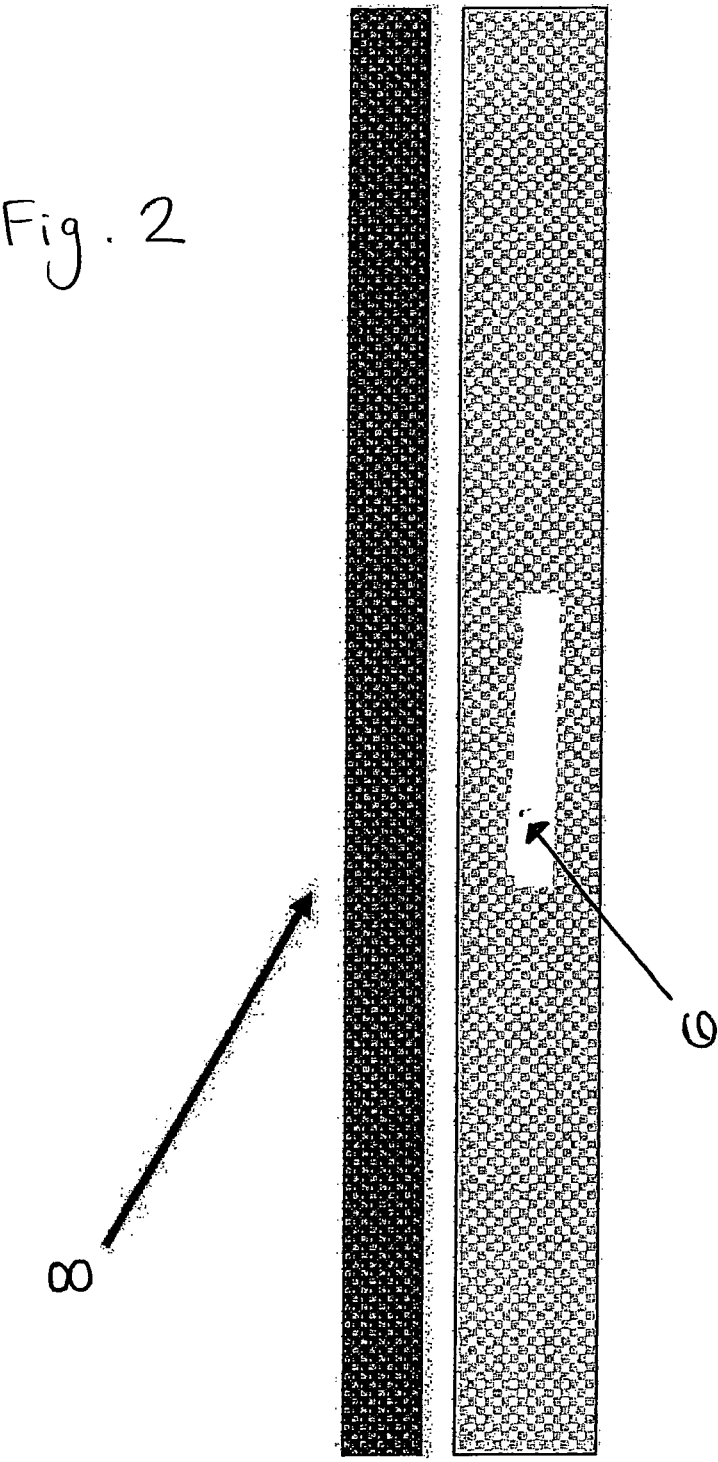
FIG. 2 shows a representation of a haemostatic material according to the invention with the adhesive layer and haemostat mixed together to form one layer.

According to another embodiment of the invention the haemostat 2 may be mixed with the adhesive layer 4 to form a combined layer 8. This is shown in FIG. 2. The combined layer 8 is located on top of the carrier layer 6.

Figure 3:
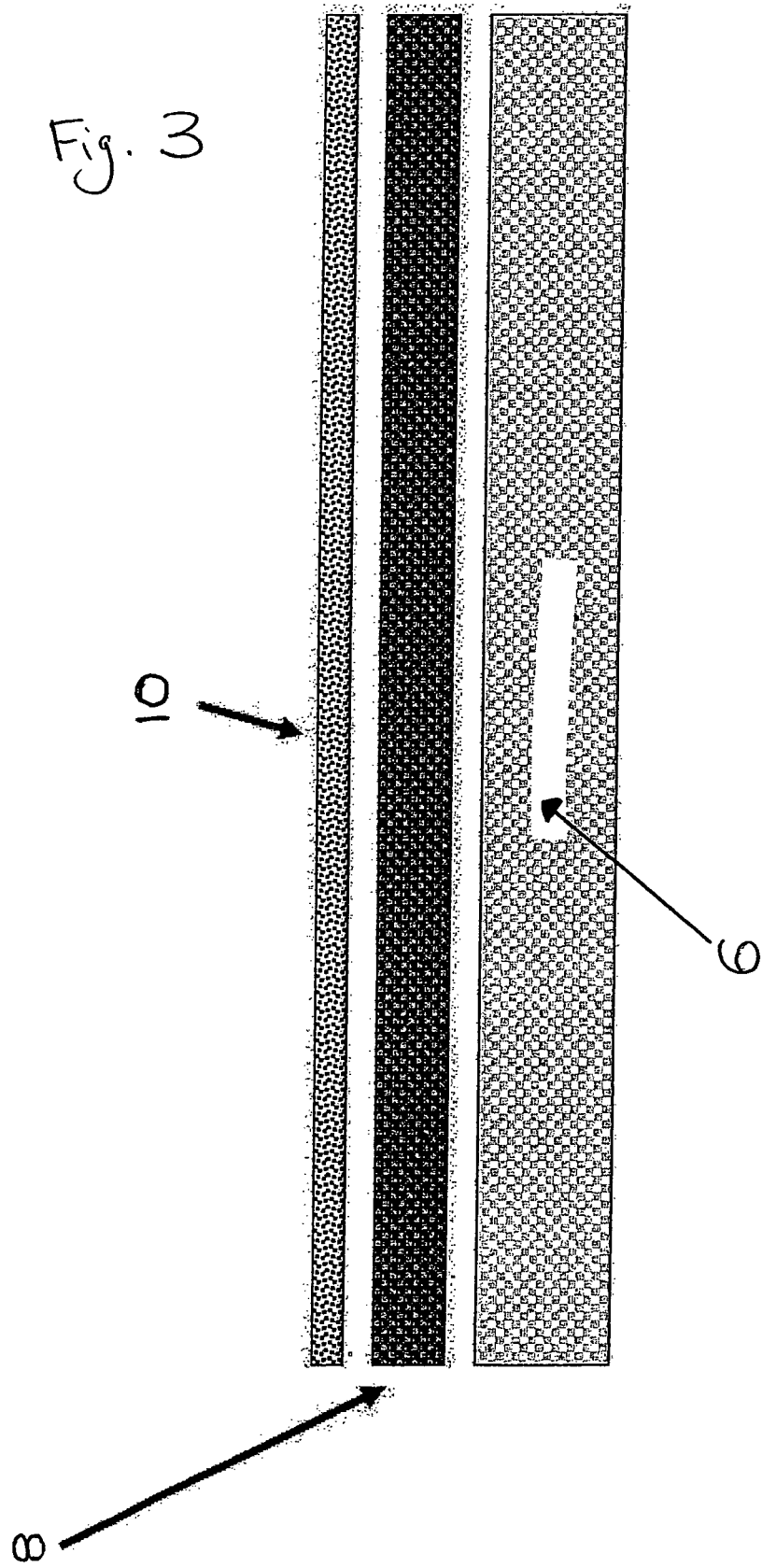
FIG. 3 shows a representation of a haemostatic material according to the invention with the adhesive layer and haemostat mixed together to form one layer and a soluble, dispersible or removable retaining layer thereon.

In addition to the embodiment depicted in FIG. 2, a soluble, dispersible or removable retaining layer 10 may be added on top of the combined layer 8. This is shown in FIG. 3. When in use in reducing or stopping blood flow from a wound, the soluble, dispersible or removable retaining layer 10 is dissolved by or dispersed in bodily fluids, exposing the combined layer 8 below it.

Figure 4:
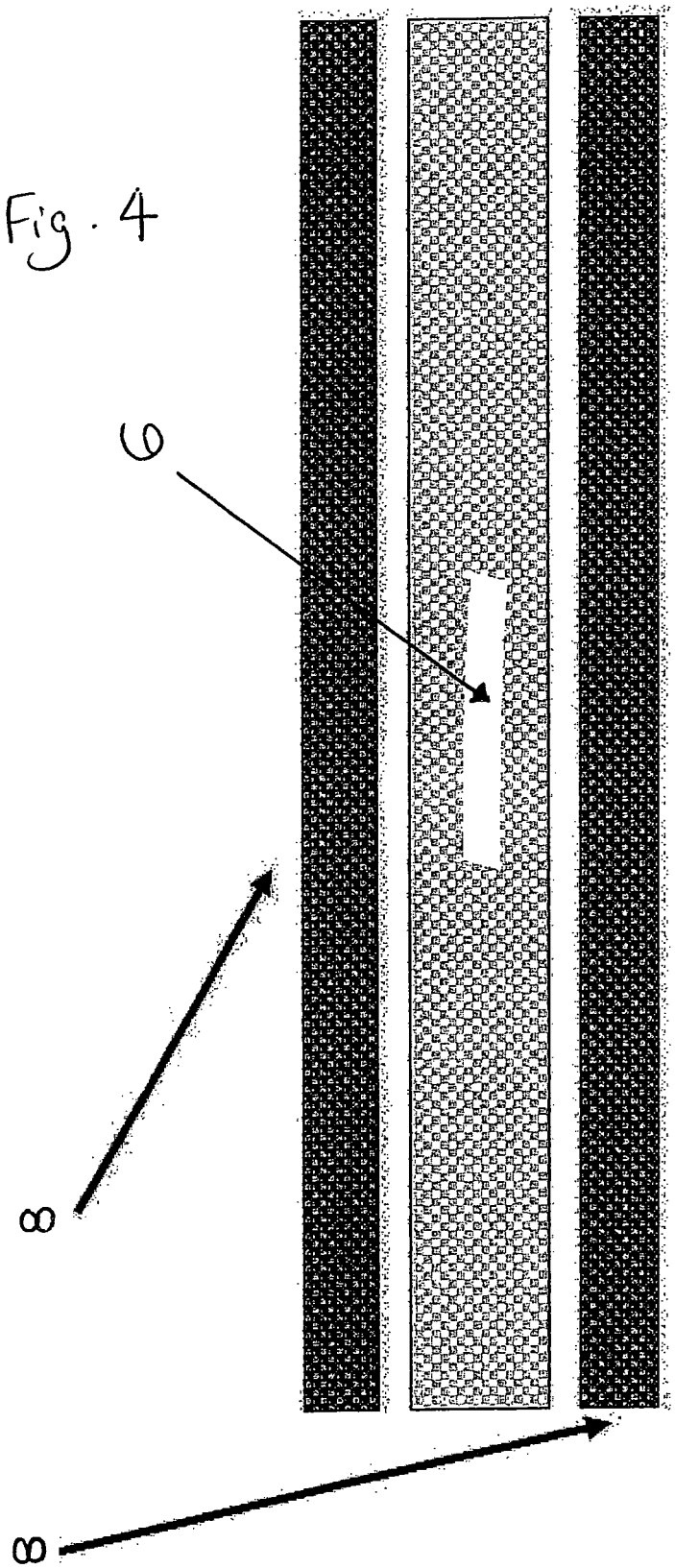
FIG. 4 shows a representation of a haemostatic material according to the invention with a mixed adhesive/haemostat layer situated on either side of the carrier layer.

In FIG. 4 it can be seen that two combined layers 8 may be employed in the haemostatic material of the invention, one above the carrier layer 6 and one below. This allows for more effective reduction and stopping of blood flow in wounds which it is possible to close around the material of the invention.

Figure 5:
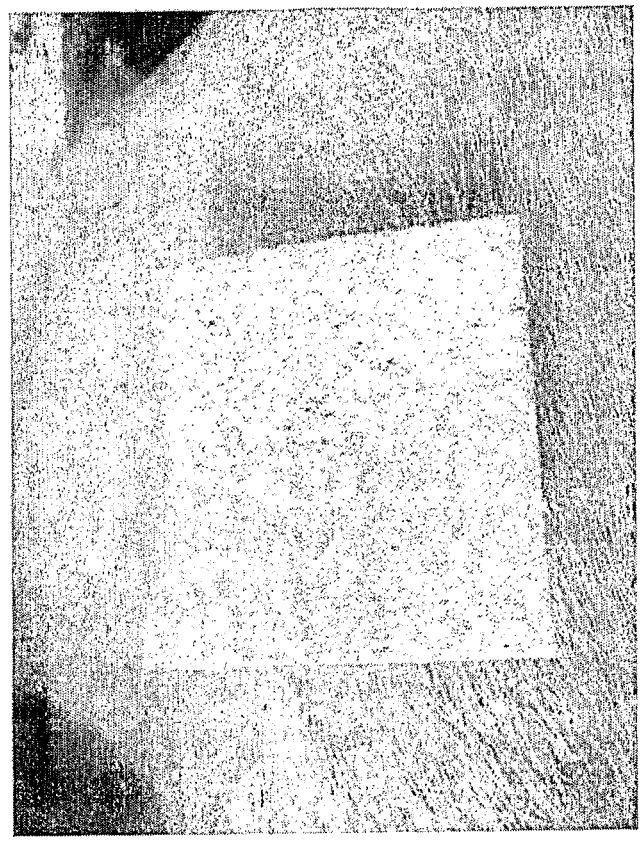
FIG. 5 shows a haemostatic material according to the invention.

FIG. 5 simply shows a view of the haemostatic material 12 of the invention which is about to be put into use in reducing or stopping blood flow from a wound.

Figure 6:
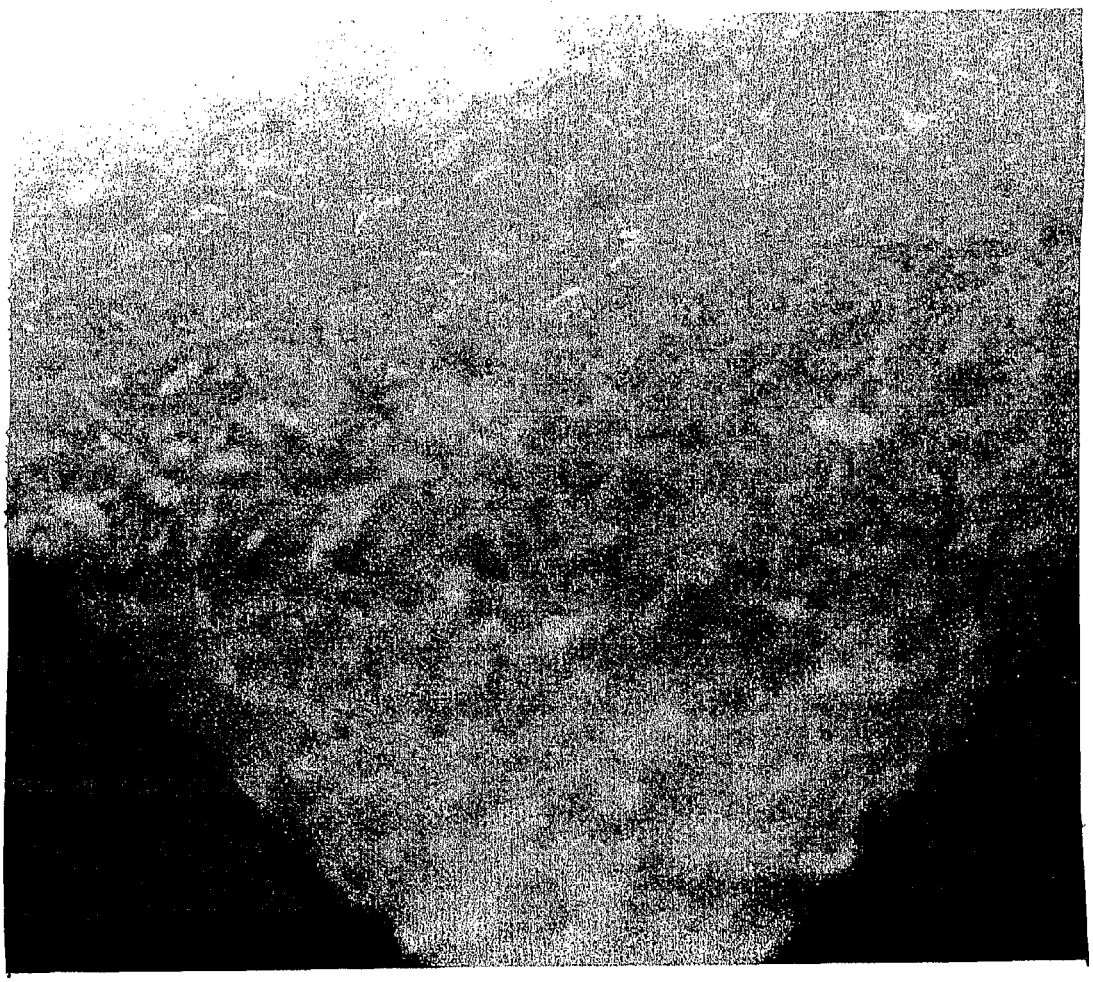
FIG. 6 shows a close-up view of a haemostatic material according to the invention.

FIG. 6 shows a close-up view of a sample of the haemostatic material 12 of the invention. The non-uniform texture of the carrier layer 6 can be clearly seen.

Figure 7:
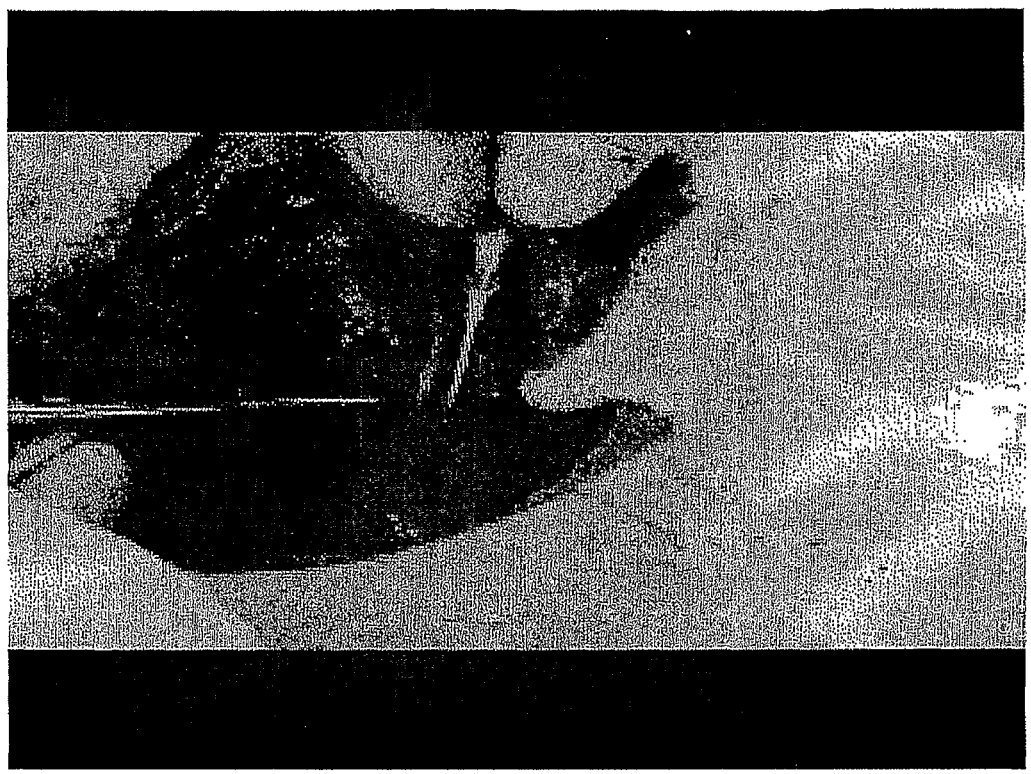
FIG. 7 shows a wound being created in a pig by a vascular puncture to the artery made using a 16 gauge needle.
Figure 8:
FIG. 8 shows a 1 cm×1 cm sheet of the haemostatic material according to the invention being applied to the wound to stem the blood flow after a specified bleed time.
Figure 9:
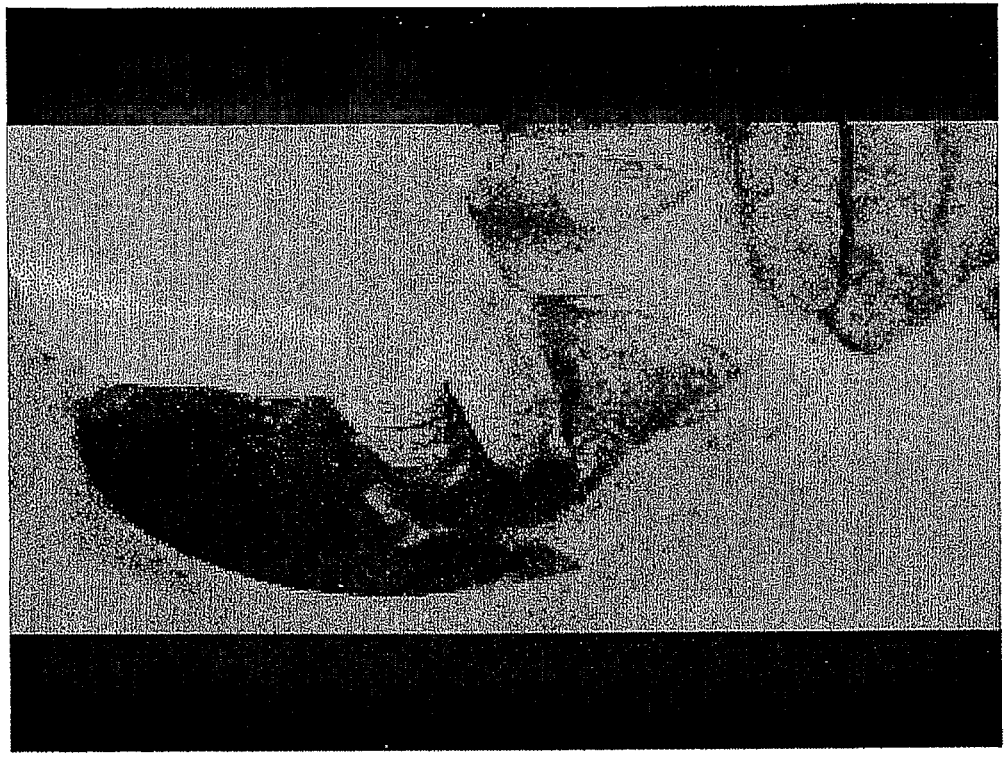
FIG. 9 shows a haemostatic material according to the invention being used in stemming blood flow in a pig. Steady compression is being applied for up to 5 minutes as required.

FIG. 7 shows a wound being created in a pig by a vascular puncture to the artery made using a 16 gauge needle. The wound is allowed to bleed for a period of time, usually about 60 seconds, before the haemostatic material 12 is applied to the wound. Then a quantity of the haemostatic material 12, in this instance a 1 cm×1 cm sheet, is applied to the wound (FIG. 8) to stem the blood flow. Steady compression is applied to the wound to ensure maximum contact between the material and the wound (FIG. 9). The compression may be maintained for up to 5 minutes as required.

Figure 10:
FIG. 10 shows a 4 cm×4 cm sheet of the haemostatic material according to the invention in use in stemming blood flow in a pig.

After the period of compression and when bleeding has been stopped, the haemostatic material 12 is left in place to prevent bleeding restarting. A 4 cm×4 cm sheet of the haemostatic material 12 is shown in this role in FIG. 10. It can be seen where the haemostatic material 12 has absorbed the blood.

Example 1

A granular haemostat (Celox) was bonded to a 120 gsm non-woven material (75% Viscose (Danufil-2) Fibres/25% polyolefin Fibres) made using a low melt copolyester resin with a melting range of 58-61° C. 40 gsm of resin was used, together with 60 gsm of Celox.

The Celox powder and bonding agent granules were blended together, and the combination powder then "scatter" coated onto the non-woven material in a continuous moving web. The web was carried on a heated moving belt which passed under, a second heated moving belt, the two belts applying heat and compression to the coated web to fuse the bonding agent and the Celox powder to the web.

The heat bonding process can be altered to change the degree of bonding. Heat, pressure and time (i.e. the speed of the moving belt) can all be varied as desired.

The resulting surface of the haemostatic material was rough and fluffy (see FIGS. 5 and 6).

The coated heat bonded web was then wound to form a roll. The resulting material was cut into 5 cm×5 cm squares, packaged and sterilised.

A hole was made in the femoral artery of a 100 lbs swine using a 16 gauge needle. The wound bled severely. The material was applied to the wound site with finger pressure for 3 minutes. The bleeding was robustly stopped. After 3 minutes the material was removed from the bleeding area. The bleeding did not restart.

Another hole was made in the femoral artery of a 100 lbs swine using a 16 gauge needle. The wound bled severely. The material was held over the wound site with minimal pressure for 30 seconds. Even with this minimal treatment the bleeding was robustly stopped. After 3 minutes the material was removed from the bleeding area. Again, the bleeding did not restart.

Example 2

A granular haemostat (Celox) was bonded to a 120 gsm non-woven material (75% Viscose (Danufil-2) Fibres/25% polyolefin Fibres) made using a low melt copolyester resin with a melting range of 58-61° C. 40 gsm of resin was used, together with 40 gsm of Celox.

The Celox powder and bonding agent granules were blended together and the combination powder then "scatter" coated onto the non-woven material in a continuous moving web. The web was carried on a heated moving belt which passed under a second heated moving belt, the two belts applying heat and compression to the coated web to fuse the bonding agent and the Celox powder to the web.

Additionally a pressure roller was applied to smooth the surface of the granules to increase the bonding to the carrier material. The resulting material was smooth.

The coated heat bonded web was then wound up to form a roll and the resulting material was cut into 5 cm×5 cm squares, packaged and sterilised.

A hole was made in the femoral artery of a 100 lbs swine using a 16 gauge needle. The wound bled severely. The material was applied to the wound site with finger pressure for 3 minutes. The bleeding was robustly stopped. After 3 minutes the material was removed from the bleeding area. The bleeding did not restart.

Example 3

A granular haemostat (Celox) was bonded to a 1 mm thick polyurethane foam using a low melt copolyester resin with a melting range of 58-61° C. 40 gsm of resin was used, together with 40 gsm of Celox.

The Celox powder and bonding agent granules were blended together and the combination powder then "scatter" coated onto the non-woven material in a continuous moving web. The web was carried on a heated moving belt which passed under a second heated moving belt, the two belts applying heat and compression to the coated web to fuse the bonding agent/Celox powder to the web.

The coated heat bonded web was then wound to form a roll and the resulting material was cut into 5 cm×5 cm squares, packaged and sterilised.

A hole was made in the femoral artery of a 100 lbs swine using a 16 gauge needle. The wound bled severely. The material was applied to the wound site with finger pressure for 3 minutes. The bleeding was robustly stopped. After 3 minutes the material was removed from the bleeding area. The bleeding did not restart.

Example 4

A granular haemostat (Celox) was bonded to a 120 gsm non-woven material using a low melt copolyester resin with a melting range of 58-61° C. 40 gsm of resin was used, together with 40 gsm of Celox.

The Celox powder and bonding agent granules were blended together and the combination powder then "scatter" coated onto the non-woven material in a continuous moving web. The web was carried on a heated moving belt which passed under a second heated moving belt, the two belts applying heat and compression to the coated web to fuse the bonding agent/Celox powder to the web. The coated heat bonded web was then wound to form a roll.

The roll was then passed back through the bonding machine and a further 40 gsm of resin and 40 gsm of Celox was applied to the other side of the fabric.

The fabric now had two haemostatic surfaces. The resulting material was cut into 5 cm×cm squares, packaged and sterilised.

Example 5

A collagen haemostat was bonded to a 120 gsm non-woven material using a low melt copolyester resin with a melting range of 58-61° C. 40 gsm of resin was used, together with 40 gsm of dry collagen granules.

The collagen and bonding agent granules were blended together and the combination powder then "scatter" coated onto the non-woven material in a continuous moving web. The web was carried on a heated moving belt which passed under a second heated moving belt, the two belts applying heat and compression to the coated web to fuse the bonding agent/Collagen powder to the web.

The coated heat bonded web was then wound to form a roll. The resulting material was cut into 5 cm×5 cm squares, packaged and sterilised.

A hole was made in the femoral artery of a 100 lbs swine using a 16 gauge needle. The wound bled severely. The material was applied to the wound site with finger pressure for 3 minutes. The bleeding had slowed but did not totally stop initially. An additional material was reapplied for a further 2 minutes. The bleeding stopped. After 10 minutes the material was removed from the bleeding area. The bleeding did not restart.

Example 6

An oxidised regenerated cellulose haemostat (ground up Surgicel) was bonded to a 120 gsm non-woven material using a low melt copolyester resin with a melting range of 58-61° C. 40 gsm of resin was used, together with 40 gsm of dry ORC granules.

The ORC and bonding agent granules were blended together and the combination powder then "scatter" coated onto the non-woven material in a continuous moving web. The web was carried on a heated moving belt which passed under a second heated moving belt, the two belts applying heat and compression to the coated web to fuse the bonding agent/ORC powder to the web.

The coated heat bonded web was then wound to form a roll. The resulting material was cut into 10 cm×2 cm squares, packaged and sterilised.

Example 7

An oxidised regenerated cellulose haemostat (ground up Surgicel) was bonded to a 120 gsm non-woven material using a meltable net (Delnet). 80 gsm of net was used, together with 40 gsm of Celox granules.

The bonding net was laid on top of the carrier material and the granules then "scatter" coated onto the non-woven material in a continuous moving web. The web was carried on a heated moving belt which passed under a second heated moving belt, the two belts applying heat and compression to the coated web to fuse the bonding agent/Celox powder to the web.

The coated heat bonded web can then be wound to form a roll. The resulting material was cut into 5 cm×5 cm squares, packaged and sterilised.

Example 8

The effectiveness of a haemostatic material according to the invention comprising Celox granules thereon was assessed by applying it to a vascular puncture site created with a 16 gauge needle in healthy Yorkshire swine.

The material used was sheets of 1 cm×1 cm and 4 cm×4 cm in size, and only one sheet of it was applied to each vascular incision. FIGS. 7-10 show the wound and subsequent treatment using the haemostatic material of the invention. The suitability of each potential subject was confirmed before his or her acceptance.

The following tables detail the procedure which was followed and the pre- and post-injury conditions of the test subjects.

|  | Prior | Treatment | 15 mins | 1 hour |
|---|---|---|---|---|
| Visual assessment | x |  |  |  |
| Measure blood pressure, etc | x |  |  |  |
| Photograph | x |  |  |  |
| Make wound |  | x |  |  |
| Apply haemostat |  | x |  |  |
| Apply compression |  | x |  |  |
| Video Treatment |  | x |  |  |
| Assess haemostasis |  | x | x | x |
| Remove Celox clot by hand |  |  |  | x |
| Irrigate to remove any residuals |  |  |  | x |
| Assessment of wound by expert |  |  |  | x |

| GENERAL | | | | | | | | |
|---|---|---|---|---|---|---|---|---|
| Method | ID | re-injury | sex | Weight (kg) | Age (weeks) | Body Temp (° C.) | MAP over 50 ml Hg | Condition |
| 1 cm × 1 cm sheet | 3 | yes | m | 90-95 | 15-20 | 36.4 | yes | good |
| 4 cm × 4 cm sheet | 4 | yes | m | 90-95 | 15-20 | 37.6 | yes | good |

| PRE-INJURY VITALS | | | | | | |
|---|---|---|---|---|---|---|
| Method | ID | Body Temp (° C.) | BP MAP | BP Systolic | BP Diastolic | Heart rate BPM |
| 1 cm × 1 cm sheet | 3 | 36.4 | 96 | 103 | 72 | 76 |
| 4 cm × 4 cm sheet | 4 | 37.2 | 63 | 98 | 74 | 69 |

| | | | | INJURY AND TREATMENT | | | |
|---|---|---|---|---|---|---|---|
| Method | ID | Wound type | Bleed Time (s) | BP after Bleed Time | treatment | Compression (mins) | Haemo achieved? |
| 1 cm × 1 cm sheet | 3 | Vascular incision | 60 | 72 | One 1 × 1 cm sheet | 5 | yes |
| 4 cm × 4 cm sheet | 4 | Vascular incision | 60 | 68 | One 4 × 4 cm sheet | 5 | yes |

| | | | 15 MINUTE ASSESSMENT | | | | |
|---|---|---|---|---|---|---|---|
| Method | ID | assessment | rebleed? | body temp (° C.) | map | Systolic | Diastolic | Heart Rate BPM |
| 1 cm × 1 cm sheet | 3 | Alive | no | 34 | 84 | 113 | 69 | 50 |
| 4 cm × 4 cm sheet | 4 | Alive | no | 33 | 92 | 104 | 76 | 60 |

| | | | 60 MINUTE/FINAL ASSESSMENT | | | | |
|---|---|---|---|---|---|---|---|
| Method | assessment | rebleed? | Body temp (° C.) | map | Systolic | Diastolic | Heart Rate BPM |
| 1 cm × 1 cm sheet 3 | Alive | no | 34.4 | 83 | 108 | 64 | 54 |
| 4 cm × 4 cm sheet 4 | Alive | no | 32 | 76 | 96 | 58 | 51 |

The assessment of haemostasis was made by visual assessment by data collection officers and confirmed with a trauma surgeon. A wound which is not haemostable (bleeding) after both 5 minutes compression and a further 2 min minutes compression counts as a 'failure'. No adverse clinical events occurred during the assessment.

The subjects survived the wounds. Only one sheet of the material of the invention was used on the wounds. No arterial re-bleeding was seen in the wounds.

Haemostasis and Survival

Haemostasis was assessed at the following points:
5 mins after initial compression
15 mins post compression No bleeding was seen from the wound at either time points. 100% haemostasis was achieved with all wounds on the pigs.

Survival was recorded at the same points:
5 mins after initial compression
15 mins post compression The results clearly demonstrate that the haemostatic material of the invention is effective when applied to a vascular puncture site.

It is of course to be understood that the present invention is not intended to be restricted to the foregoing examples which are described by way of example only.

The invention claimed is:

1. A haemostatic material comprising:
a carrier layer comprising a non-woven material, woven gauze, a film, a foam or a sheet gel, and
a wound contact layer being a single layer comprising a mixture of at least one haemostat and an adhesive, the wound contact layer being bonded directly to the carrier layer,
wherein the at least one haemostat is in a form selected from the group consisting of: particulate, granular, powder, flake, and short fibrous, wherein said haemostat comprises a chitosan salt, and
wherein the haemostat or adhesive is sufficiently water sensitive to weaken the bond between the haemostat and the adhesive upon contact with a fluid, such that when the wound contact layer is wet with blood a portion of the haemostat will remain at the wound site if the carrier layer is removed.

2. A haemostatic material according to claim 1 wherein both surfaces of the carrier layer are at least partially coated with haemostat.

3. A haemostatic material according to claim 1 further comprising a material which is degradable in the body.

4. A haemostatic material according to claim 1 wherein the haemostat comprises two or more haemostats.

5. A haemostatic material according to claim 1, comprising wound contact layer on an upper and lower surface of the carrier layer.

6. A haemostatic material according to claim 1, further comprising a soluble, dispersible or removable retaining layer on top of the wound contact layer.

7. A haemostatic material according to claim 6, wherein the soluble, dispersible or removable retaining layer is formed from a material susceptible to metabolisation within a human or animal body.

8. A haemostatic material according to claim 1, wherein the chitosan salt comprises one or more salts selected from the group consisting of chitosan acetate, chitosan lactate, chitosan succinate, chitosan malate, and chitosan acrylate.

9. A haemostatic material according to claim 8, wherein the chitosan salt comprises chitosan succinate.

10. A haemostatic material according to claim 1 wherein the chitosan salt constitutes at least about 5% by weight of the haemostat.

11. A haemostatic material according to claim 1, wherein the haemostat is granular.

12. A haemostatic material according to claim 1 further comprising a medical surfactant.

13. A haemostatic material according to claim 12, wherein the medical surfactant constitutes from about 0.001 to about 10% by weight of the haemostat.

14. A haemostatic material according to claim 12 wherein the medical surfactant comprises one or more components selected from the group consisting of block copolymers based on ethylene oxide and propylene oxide, fatty acids, fatty acid salts, silicone based surfactants and emulsifiers.

15. A haemostatic material according to claim 14, wherein the medical surfactant is a fatty acid selected from lauric acid and oleic acid.

16. A haemostatic material according to claim 1 further comprising at least one inert material.

17. A haemostatic material according to claim 16, wherein the at least one inert material comprises one or more selected from the group consisting of cellulose, fumed silica, sand, clay, alginate, microcrystalline cellulose, oxidised regenerated cellulose, polyethylglycol, guar gum, xanthan gum, chitosan, chitosan derivatives, chitin, sucrose, lactose, pectin, carboxymethylcellulose, ground corn meal, collagen, gelataine, polyvinylalcohol, acrylic acid, acrylate (co)polymers, crosslinked acrylic acid-based polymers, barium sulphate, clay, lactose, sucrose, starch, and combinations of any two or more thereof.

18. A haemostatic material according to claim 16 wherein the inert material constitutes up to about 95% by weight of the haemostat.

19. A haemostatic material according to claim 1 wherein the haemostat comprises particles which cannot pass through a 200 mesh sieve.

20. A haemostatic material according to claim 1 wherein the adhesive layer comprises a bonding agent wherein the bonding agent is a meltable material.

21. A haemostatic material according to claim 1 wherein the carrier layer is degradable in a human or animal body.

22. A haemostatic material according to claim 1 wherein the carrier layer comprises a viscose non-woven material.

23. A haemostatic material according to claim 1 wherein the carrier layer comprises a material selected from the group consisting of woven gauze, a film, foam, and a sheet gel.

24. A haemostatic material according to claim 12 wherein the particle size of the haemostat and the particle size of the medical surfactant are equivalent.

25. A haemostatic material according to claim 1 wherein the haemostat has a pH of from about 3.5 to about 8.0.

26. A haemostatic material according to claim 1 further comprising an absorbent layer.

27. A haemostatic material according to claim 1 wherein the material comprises part of a first aid plaster.

28. A haemostatic material according to claim 1 wherein the material further comprises a quantity of a substance which is opaque to X-rays.

29. A haemostatic wound dressing comprising:
a dressing and
a haemostatic material comprising
a carrier layer comprising a non-woven material, woven gauze, a film, a foam or a sheet gel, and
a wound contact layer being a single layer comprising a mixture of at least one haemostat and an adhesive, the wound contact layer being bonded directly to the carrier layer,
wherein the at least one haemostat is in a form selected from the group consisting of: particulate, granular, powder, flake, and short fibrous,
wherein said haemostat comprises a chitosan salt, and wherein the haemostat or adhesive is sufficiently water sensitive to weaken the bond between the haemostat and the adhesive upon contact with a fluid, such that when the wound contact layer is wet with blood a portion of the haemostat will remain at the wound site if the carrier layer is removed.

30. A haemostatic material according to claim 1, wherein the chitosan salt is of an organic acid.

31. A haemostatic material for application to a wound site, comprising:
a carrier layer comprising a non-woven material having an upper surface and a lower surface; and
a haemostatic wound contact layer adhered to the upper surface of said carrier layer,
said haemostatic wound contact layer comprising a mixture of chitosan salt haemostat and a bonding agent, said mixture being applied directly to said upper surface of said carrier layer by heat, said wound contact layer being a single layer,
said chitosan salt haemostat being provided in a physical form selected from the group consisting of powder, particulate, granular, flake and fiber,
said bonding agent being provided in a granular form, said bonding agent being at least partially water soluble,
wherein said haemostat and said bonding agent are mixed together prior to application to said carrier material, scatter coated onto said carrier material, and adhered to said carrier material by heat thus forming a water soluble wound contact layer on said upper surface of said carrier material,
said wound contact layer being sufficiently water sensitive to weaken the adhesive bonds when the wound contact layer is wet thus releasing the haemostat from the wound contact layer for therapeutic effect and whereby at least a portion of the haemostat remains in the wound when the carrier layer is removed.

* * * * *